United States Patent
Lemaire et al.

(10) Patent No.: US 9,359,280 B2
(45) Date of Patent: Jun. 7, 2016

(54) PROCESS FOR PREPARING A CARBOXYLIC ACID FROM A DIOL OR FROM AN EPOXIDE BY OXIDATIVE CLEAVAGE

(71) Applicants: SOCIETE INTEROLEAGINEUSE D'ASSISTANCE ET DE DEVELOPPEMENT (S.I.A.), Paris (FR); UNIVERSITÉ CLAUDE BERNARD LYON 1, Villeurbanne (FR); CENTRE NATIONAL DE LA RECHERCHE SCIENTIFIQUE (CNRS), Paris (FR); OLEON, Venette (FR)

(72) Inventors: Marc Lemaire, Villeurbanne (FR); Estelle Metay, Vaulx en Velin (FR); Marc Sutter, Villeurbanne (FR); Julien Debray, Glenac (FR); Yann Raoul, Soissons (FR); Nicolas Duguet, Meyzieu (FR)

(73) Assignees: SOCIETE INTEROLEAGINEUSE D'ASSISTANCE ET DE DEVELOPPEMENT, Paris (FR); UNIVERSITE CLAUDE BERNARD LYON 1, Villeurbanne (FR); CENTRE NATIONAL DE LA RECHERCHE SCIENTIFIQUE, Paris (FR); OLEON, Venette (FR)

( * ) Notice: Subject to any disclaimer, the term of this patent is extended or adjusted under 35 U.S.C. 154(b) by 0 days.

(21) Appl. No.: 14/418,562

(22) PCT Filed: Jul. 30, 2013

(86) PCT No.: PCT/FR2013/051842
§ 371 (c)(1),
(2) Date: Jan. 30, 2015

(87) PCT Pub. No.: WO2014/020281
PCT Pub. Date: Feb. 6, 2014

(65) Prior Publication Data
US 2015/0210623 A1 Jul. 30, 2015

(30) Foreign Application Priority Data
Jul. 31, 2012 (FR) ...................................... 12 57421

(51) Int. Cl.
*C07C 51/367* (2006.01)
*C07D 317/12* (2006.01)
*C07C 51/23* (2006.01)

(52) U.S. Cl.
CPC ............... *C07C 51/367* (2013.01); *C07C 51/23* (2013.01); *C07D 317/12* (2013.01)

(58) Field of Classification Search
None
See application file for complete search history.

(56) References Cited

U.S. PATENT DOCUMENTS

| | | | | |
|---|---|---|---|---|
| 4,006,173 | A | * | 2/1977 | Zeidler ........................ 554/136 |
| 2008/0245995 | A1 | * | 10/2008 | Bastioli ................. C07C 51/245 252/182.12 |
| 2012/0302778 | A1 | * | 11/2012 | Bieser .................... C07C 51/245 554/132 |
| 2012/0323028 | A1 | * | 12/2012 | Bieser ..................... C07C 51/09 554/136 |
| 2013/0131379 | A1 | * | 5/2013 | Lemaire et al. ............... 562/525 |

FOREIGN PATENT DOCUMENTS

| | | |
|---|---|---|
| DE | 2 106 913 | 9/1972 |
| FR | 2 086 521 | 12/1971 |
| FR | 2 957 074 | 9/2011 |
| WO | WO 94/10122 | 5/1994 |
| WO | WO 2007/039481 | 4/2007 |
| WO | WO 2008/138892 | 11/2008 |
| WO | WO 2011/046883 | 4/2011 |
| WO | WO 2011/080296 | 7/2011 |

OTHER PUBLICATIONS

Fujitani et al., J. Oleo Sci. 58, (12) 629-637 (2009).*
Coin et al., Eur. J. Org. Chem. 2001,735-739.*
Kumar et al., Synlett (2009), (5), 739-742.*
Database CAPLUS Chemical Abstracts Service, Columbus, Ohio, US; Database Accession No. 2013:273293, Abstract of Barati et al., Synlett (2013), 24(1), 90-96.*
International Preliminary Report on Patentability dated Feb. 3, 2015, issued in corresponding International Application No. PCT/FR2013/051842 & English translation of Written Opinion.
International Search Report for PCT/FR2013/051842, mailed Nov. 22, 2013, Lacombe, Céline, 2 pages.
S. Dakdouki, "On-Column Solvent-Free Oxidative Cleavage Reactions of Vicinal Diols by Silica Gel and Paraperiodic Acid: Application to In-Situ Sequential Oxidation and Knoevenagel Reactions", Eur. J. Org. Chem., pp. 780-784, (2012), 5 pages.
D. Bandyopadhyay et al., "Bismuth Nitrate-Induced Microwave-Assisted Expeditious Synthesis of Vanillin from Curcumin", Organic and Medicinal Chemistry Letters, 2:15, (2012), 4 pages.
K. Fujitani et al., "Preparation of Polycarboxylic Acids by Oxidative Cleavage with Oxygen / Co—Mn—Br System", Journal of OLEO Science, vol. 58, No. 12, pp. 629-637, (2009), 9 pages.

* cited by examiner

*Primary Examiner* — Karl J Puttlitz
(74) *Attorney, Agent, or Firm* — Nixon & Vanderhye P.C.

(57) ABSTRACT

A process for preparing a carboxylic acid, by oxidative cleavage of at least one vicinal diol, or an epoxide, wherein the reaction is carried out in the presence of a catalyst and of an oxidizing agent and in the absence of solvent.

15 Claims, No Drawings

PROCESS FOR PREPARING A CARBOXYLIC ACID FROM A DIOL OR FROM AN EPOXIDE BY OXIDATIVE CLEAVAGE

This application is the U.S. national phase of International Application No. PCT/FR2013/051842, filed 30 Jul. 2013 which designated the U.S. and claims priority to FR Application No. 1257421, filed 31 Jul. 2012; the entire contents of each of which are hereby incorporated by reference.

The invention relates to a process for preparing carboxylic acids, more especially carboxylic acids having one or two acid functions, by oxidative cleavage of at least one diol or an epoxide.

Oxidative cleavage of olefins can generally be conducted in one or two steps, either directly from olefins, or following a preliminary step of hydroxylation or epoxidation of these compounds.

The one-step reaction generally used is ozonolysis. This technique, however, is costly and causes numerous safety issues.

There are also numerous methods for oxidative cleavage of olefins such as oleic acid, which use transition metal-based catalysts associated with various oxidizing agents such as $Re_2O_7/H_2O_2$, $RuCl_3/H_2O_2$, $NaIO_4$, Ru(complex)/C, $NiCl_2$/NaOCl, $InCl_3$/$^tBuOOH$, polyoxometalate/$H_2O_2$, or the "Bismuth complex", used in organic medium, under an air or pure oxygen atmosphere at a more or less high temperature. However, most of these methods present a risk from an environmental point of view, in particular reactions using nickel salts known to be highly toxic, or present risks such as fire, such as the use of pure oxygen and organic solvents which promote combustion.

There are also two-step methods, for example metathesis on fatty acids such as oleic acid, followed by oxidative cleavage of the products obtained, but undesired by-products are obtained, such as 1-decene.

There are also two-step methods, such as dihydroxylation of olefins, especially of unsaturated fatty acids, offering the advantage with respect to the direct access pathway from olefins or unsaturated fatty acids of producing a purer end product, oxidative cleavage can therefore be considered directly from diol.

Document FR2086521 discloses, in this sense, oxidative cleavage of various vicinal diols, including oleic acid diol, with potassium monopersulphate and in the presence of a catalytic quantity of nickel (20 mol %). This technology uses nickel salts and remains environmentally toxic.

Patent application U.S. Pat. No. 4,006,173 discloses a continuous cleavage method using cobalt or ruthenium complexes under an atmosphere with pure oxygen and in the presence of solvent.

The prior art also mentions the use of bleach to obtain oxidative cleavage of a vicinal diol (patent application FR2957074), or cobalt catalysis, for oxidative cleavage of diols, in the presence of an oxidizing agent (hydrogen peroxide, peroxides, ozone, etc.), under an atmosphere including oxygen (patent applications DE2106913 and WO9410122).

In similar technologies, oxidative cleavage of various vicinal diols or of unsaturated fatty acids, including 9,10-dihydroxystearic acid and oleic acid, is described as being conducted in the presence of a catalytic quantity of catalyst (tungsten, cobalt, etc.) and of hydrogen peroxide under oxygen atmosphere (WO2007/039481 A1).

WO2008/138892 and WO2011/080296 both disclose a method for preparing monocarboxylic acids and triglycerides in the presence of solvent.

All these above-mentioned methods, conducted directly on olefins, diols or epoxides, use oxidizing agents or solvents that are hazardous and toxic for the environment and that are also expensive and difficult to implement from the point of view of safety and complexity due to a plurality of steps.

There is therefore a need to develop a technology allowing oxidative cleavage of vicinal diols or unsaturated fatty acids (olefins) in order to obtain aldehydes or preferably, carboxylic acids, less difficult to implement, exhibiting a high conversion rate, economically accessible and/or more environmentally friendly.

This invention therefore relates to a method for preparing a carboxylic acid, or an aldehyde, by oxidative cleavage of at least one olefin, a vicinal diol, or an epoxide, the reaction being conducted in the presence of a catalyst, an oxidizing agent and in the absence of solvent.

The invention has the advantage of not using solvents. This reduces the reaction costs, limits the risk of polluting the environment and the danger of the reaction. Furthermore, the invention can also be used to prepare aldehydes or advantageously carboxylic acids in a single step or by combining the dihydroxylation step and the oxidative cleavage step in the same reactor when the reaction is conducted directly from olefins.

Preferably, the invention relates to a method for preparing a carboxylic acid, by oxidative cleavage of at least one vicinal diol, or an epoxide, the reaction being conducted in the presence of a catalyst, an oxidizing agent and without addition of solvent.

The oxidative cleavage reaction is preferably conducted on pure vicinal diols or epoxides, in order to obtain acids also having a high degree of purity. The purity of the product obtained may therefore be greater than or equal to 95% by weight, preferably greater than or equal to 99%.

The term "solvent" means the organic compounds containing at least one carbon atom and inorganic compounds containing no carbon atoms which are capable of dissolving or diluting at least one of the products used or obtained by the method of the invention.

The expression "absence of solvent" should be understood in its most common sense as not excluding the presence of a small, or "trace", quantity of solvent. Such a quantity may for example be quantified as being less than or equal to 10% by weight of the reaction medium, preferably less than 1%, or less than 0.1%.

The oxidative cleavage reaction used in the method of the invention is therefore advantageously conducted in the absence of solvent, i.e. without adding organic solvent or inorganic solvent, including water, to any of the steps in the method. It can be used to obtain at least one, and preferably two, compounds such as carboxylic acids, aldehydes or other oxygen-containing compounds such as oxacycloalkanes. In particular, the production of carboxylic acid is considered.

The term "carboxylic acid" means any compound having a structure of varied nature, linear, branched or cyclic, having at least one carboxylic acid function.

The term "aldehyde" means any compound having a structure of varied nature, linear, branched or cyclic, having at least one aldehyde function.

Preferably, the reaction is conducted under an atmosphere comprising oxygen, the oxygen then being the oxidizing agent of the reaction.

Advantageously, the reaction is conducted in the presence of air, or a mixture of gases including oxygen in proportion similar to air and inert gases, the oxygen in the air being the oxidizing agent of the reaction. The use of oxygen in the air as oxidizing agent is less dangerous and avoids the need to add a product which could be toxic or difficult to control or recycle. A particular aspect of the invention is therefore a method not using an oxidizing agent other than air or a mixture of equivalent dangerousness.

Preferably, the reaction is conducted in the presence of a catalyst based on ruthenium, cerium, palladium, iron, copper, nickel, rhenium, manganese, rhodium, cobalt, vanadium, molybdenum, gold, tungsten, lead, platinum or a mixture thereof.

Preferably, the catalyst is of formula $M(OH)_x/Support$, wherein M is a metal as defined above, x is an integer from 0 to 8, and wherein the support is selected from the supports traditionally used in heterogeneous catalysis. Thus, the metal M may be deposited on alumina, zirconia, carbon, silica, a zeolite or a mixture thereof. Preferably, the catalyst is selected from catalysts of low toxicity that are easy to recycle. It is also advantageous to use a catalyst in solid or heterogeneous form, during the method according to the invention.

Advantageously, M is a metal selected from the group consisting of palladium, iron, copper, nickel, rhenium, manganese, rhodium, platinum, vanadium, molybdenum, gold, tungsten, lead and a mixture thereof Even more advantageously, the catalyst used is a catalyst based on ruthenium, iron, copper or palladium.

Preferably, x is a number, integer or not, from 1 to 8, more especially from 1 to 4 and preferably from 1 to 3.

Preferably, the catalyst used is a ruthenium on alumina-based catalyst of formula $Ru(OH)_x/Al_2O_3$.

Preferably, the proportion of catalyst used is from 0.001 mol % to 50 mol % relative to the substrate and/or from 0.001% to 50% by weight relative to the support. Preferably, the proportion of catalyst used is from 0.01 mol % to 50 mol % relative to the substrate and/or from 0.01% to 50% by weight relative to the support.

Advantageously, the metal used is ruthenium, iron, copper or palladium.

The catalyst load used may range from 0.1 ppm to 100 ppm (weight). Preferably it is selected from 1 ppm to 50 ppm, more particularly from 5 ppm to 15 ppm, for example 10 ppm.

Advantageously, the reaction is conducted at a pressure from $10^{-3}$ mbar to 15 bar, preferably from 4 bar to 10 bar, more preferably 8 bar±0.2 bar.

Conducting the reaction at such pressures offers in particular better control and/or better yield of the reaction.

Advantageously, the reaction is conducted at a temperature from 0° C. to 200° C., preferably from 90° C. to 160° C., more preferably from 90° C. to 110° C.

Conducting the reaction according to the invention at such temperatures offers better control and/or better yield of the reaction.

Advantageously, the olefin used in the reaction comprises at least 10 carbon atoms, preferably from 10 to 30 carbon atoms, and has the following formula (I):

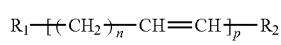
(I)

and, the diol used comprises at least 10 carbon atoms, preferably from 10 to 30 carbon atoms, preferably from 1 to 24 carbon atoms and has the following formula (II):

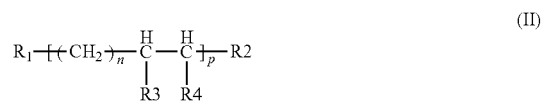

wherein,
p is an integer from 1 to 6, preferably from 1 to 3;
n is an integer from 1 to 28, more preferably from 1 to 12;
$R_1$ and $R_2$ represent independently:
an alkyl or hydroxyalkyl group having from 1 to 27 carbon atoms, preferably from 1 to 12 carbon atoms,
a hydrogen atom, or
a $—(CH_2)_m—CO_2A$ group wherein m, which can be identical or different in $R_1$ et $R_2$, is an integer from 1 to 26, preferably from 1 to 11, and A represents a hydrogen atom or an alkyl group having from 1 to 4 carbon atoms or an alkali cation, or $R_1$ et $R_2$ form together an alkylene $—(CH_2)_{m'}—$ group wherein m' is an integer between 2 and 10, preferably between 2 and 6, and $R_3$ et $R_4$ form together a —O— (epoxy) bond, or each represent a hydroxyl group.

In this case, an "alkyl group" means a linear or branched, preferably linear, saturated hydrocarbon chain.

In this case, a "hydroxyalkyl group" means an alkyl group in which at least one of the hydrogen atoms is replaced by a hydroxy (—OH) group.

The method according to the invention is generally useful for oxidative cleavage of diols derived from mono-unsaturated or poly-unsaturated acids and their derivatives such as, for example, the corresponding fatty acid esters, in particular long chain (having more than 10 carbon atoms, preferably from 10 to 30 carbon atoms), preferably from a natural source and in particular oilseed plants, for example soya bean oil, sunflower oil, rapeseed oil, linseed oil, olive oil, castor oil, peanut oil, or palm oil.

Examples of mono-unsaturated acids include myristoleic acid (9-tetradecenoic acid), palmitoleic acid (9-hexadecenoic acid), oleic acid (9-octadecenoic acid), ricinoleic acid (12-hydroxy-9-octadecenoic acid), gadoleic acid (11-eicosenoic acid), erucic acid (13-docosenoic acid), nervonic acid (15-tetracosenoic acid).

Examples of poly-unsaturated acids include linoleic acid (9,12-octadecadienoic acid), alpha-linolenic acid (9,12,15-octadecatrienoic acid), gamma-linolenic acid (6,9,12-octadecatrienoic acid), di-homo-gamma-linolenic acid (8,11,14-eicosatrienoic acid), arachidonic acid (5,8,11,14-eicosatetraenoic acid), timnodonic acid (5,8,11,14,17-eicosapentaenoic acid), cervonic acid (4,7,10,13,16,19-docosahexaenoic acid).

This method can also be applied to dimeric or trimeric compounds resulting from the dimerization or trimerization of fatty acids or fatty acid esters present in rapeseed, linseed, olive, castor or peanut oils.

This method is particularly suitable for oxidative cleavage of oleic acid diol (compound of above-mentioned formula I wherein p and n equal 1, $R_1$ represents a $—(CH_2)_6—CH_3$ group, $R_2$ represents a $—(CH_2)_7—COOH$ group and $R_3$ and $R_4$ represent an alcohol function) in pelargonic acid and azelaic acid.

The starting material used in the method according to the invention may advantageously be a mixture of compounds, for example a mixture of olefins, in particular a mixture of fatty acids or their hydroxylated derivatives.

This method is also useful for oxidative cleavage of diols derived from cyclic alkenes and in particular the diol of cyclohexene to prepare adipic acid whose industrial application for the manufacture of nylon is well known.

When one of the substituents $R_1$ et $R_2$ represents a —$(CH_2)_m$—$CO_2A$ group (where A represents a hydrogen atom or an alkyl group having from 1 to 4 carbon atoms and m is an integer from 1 to 26, preferably from 5 to 9) and the other substituent represents an alkyl group having from 1 to 27 carbon atoms, preferably from 1 to 12, preferably from 5 to 9, oxidative cleavage of the compound of formula (I) yields a mixture of mono-carboxylic acid and di-carboxylic acid. This is the case for example when the starting material is oleic acid and a mixture of pelargonic acid and azelaic acid is obtained. Oxidative cleavage may also lead to a mixture of monocarboxylic acid and semi-ester. This is the case when the starting material is an alkyl oleate and a mixture of pelargonic acid and mono-alkyl azelate is obtained.

When the groups $R_1$ and $R_2$ simultaneously represent a group of formula —$(CH_2)_m$—$CO_2A$ (where m may be different in each of the substituents $R_1$ et $R_2$), oxidative cleavage results in a mixture of dicarboxylic acids or even a single di-carboxylic acid when the initial diol is symmetrical, i.e. when $R_1$ represents a —$(CH_2)$—$CO_2A$ group and $R_2$ represents a —$(CH_2)$—$CO_2A$ group, with n equal to 1.

Thus, according to a particularly advantageous characteristic of the invention, the initial diol has the formula (I) wherein:
$R_1$ represents:
a —$(CH_2)_{n-1}$—$CO_2A$ group wherein n is an integer between 6 and 9 and A represents a hydrogen atom or an alkali cation;
$R_2$ represents:
a —$(CH_2)_n$—$CO_2A$ group wherein n, which is identical in $R_1$ and $R_2$, is an integer between 6 and 9 and A represents a hydrogen atom or an alkali cation; and p is preferably equal to 1.

Preferably, the starting material is an ω-unsaturated or ω-dihydroxylated fatty acid, i.e. a fatty acid consisting of or comprising an acyclic carbon chain, the latter comprising an unsaturation or a double vicinal hydroxylation at the end of the chain such as methyl 9-decenoate and the corresponding dihydroxylated compound.

Preferably, the starting material is oleic acid and/or 9,10-dihydroxystearic acid.

According to a particularly advantageous aspect of the invention, when the starting material is an olefin, the method comprises an additional preliminary step of hydroxylation of the olefin used. This step can be conducted using electrophilic oxidizing agents such as potassium permanganate or osmium tetroxide, or by hydrolysing oxacyclopropanes (epoxides). Advantageously, this step can be used to purify the diol obtained and conduct the oxidative cleavage reaction according to the method of the invention on a purified diol in order to obtain high-purity carboxylic acids.

Advantageously, the method according to the invention can be used to obtain a dicarboxylic acid, a dialdehyde and/or an aldehyde/acid, saturated or unsaturated.

According to another advantageous aspect of the invention, the method can be used to obtain an aldehyde or, even more advantageously, an unsaturated carboxylic acid. Such compounds can be obtained for example through the use of unsaturated vicinal diols as starting materials. These can be obtained, for example, by selective epoxidation of an olefin with several unsaturations.

Preferably, the method according to the invention can be used to prepare a dicarboxylic acid. Preferably, it can be used to prepare a monocarboxylic acid and a dicarboxylic acid.

Advantageously, the carboxylic acid obtained has the following formula (II):

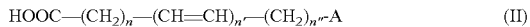

$$\text{HOOC—}(CH_2)_n\text{—}(CH=CH)_{n'}\text{—}(CH_2)_{n''}\text{-A} \qquad (II)$$

wherein
n, n' and n" are identical or different, chosen independently from each other, from 0 to 10,
A corresponds to a hydrogen atom, to a carboxylic acid function —(COOH), and
said carboxylic acid having from 2 to 16 carbon atoms, preferably from 3 to 12 carbon atoms, preferably 5, 6, 7, 8, 9 or 10 carbon atoms.

According to a preferred embodiment of the invention, the reaction products obtained from oleic acid, its diol or epoxide derivative, are pelargonic acid and azelaic acid.

An advantageous aspect of the method is a high conversion rate into carboxylic acid and/or aldehyde, in particular greater than 90% and more particularly greater than 99%.

Another advantageous aspect is a mass yield of bifunctional compounds such as dicarboxylic acids, dialdehydes or aldehydes/acids, greater than 35%, preferably greater than 40%.

According to another preferred embodiment of the invention, the diol used is cyclohexane diol and preferably, the method according to the invention can be used to obtain adipic acid.

According to an alternative method when the starting material is an olefin, carboxylic acid or aldehyde is obtained in a single reaction step.

The invention will be better understood on reading the examples which are given solely by way of example and not limiting in any way.

EXAMPLE 1

Synthesis of Pelargonic Acid and Azelaic Acid from Oleic Acid by Oxidative Cleavage 1.a. Synthesis of 9,10 dihydroxystearic acid by di-hydroxylation of oleic acid 25 mL of 30% v/v hydrogen peroxide (248 mmol, 1.4 eq.), 91.3 mL of formic acid (2.42 mol, 13.7 eq.) are incorporated in a mixture and cooled to 0° C., then 50 g of 90% pure oleic acid (159 mmol) are added drop by drop. The purity of the acid is determined by GC/MS analysis of the corresponding methyl ester.

The resulting mixture is then heated to 40° C. for 8 h, and allowed to rest at room temperature overnight.

The water and the formic acid are partially removed at reduced pressure until an oil is obtained.

The oil is mixed in 150 mL of 1 N potassium hydroxide (KOH), then heated to 90 ° C. for 1 h.

The pH of the solution is adjusted to 2 by adding concentrated hydrochloric acid (37 wt %).

The oil phase obtained is separated using a dropping funnel and washed with 100 mL of water. 59 g of an oil are obtained.

In order to analyse the oil, it is recrystallised in hexane, producing pure 9,10-dihydroxystearic acid in the form of a white solid.

Mp=130° C. to 132° C., FTIR analysis, $^1H$ and $^{13}C$ MNR in MeOD and GC/MS analysis of the methyl ester in accordance with the literature (lit. 130° C. to 131° C.).

1.b. Synthesis of the Catalyst of Formula Ru(OH)$_x$/Al$_2$O$_3$:

Powdered alumina (2 g) is added (after calcination at 550° C. for 3 hours) to an aqueous solution of RuCl$_3$ at room temperature (8.3 mM). After 15 min, the pH is adjusted to 13 by adding a solution of NaOH (1M).

The mixture is then stirred at room temperature for 24 hours. The solid is then filtered and washed with water and dried in vacuo to produce 2.1 g of Ru(OH)$_x$/Al$_2$O$_3$, (1≤x≤3).

1.c. Synthesis of mono- and di-carboxylic acid from 9,10-dihydroxystearic acid, by oxidative cleavage:

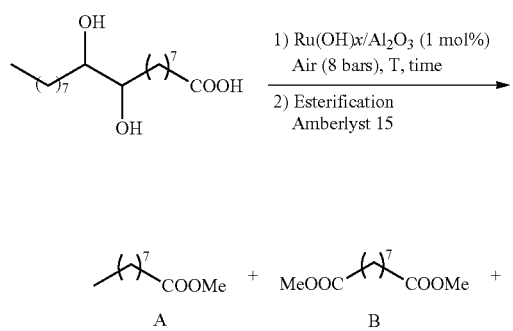

2 g (13.7 mmol) of 9,10-dihydroxystearic acid are added in the presence of 1 mol % of Ru(OH)$_x$/Al$_2$O$_3$ (1≤x≤3) in an autoclave. The mixture is heated to 150° C. for 15 h under 8 bar air pressure. After 15 h, the reaction medium is diluted in 10 mL of methanol then filtered.

To allow analysis by gas chromatography/mass spectrometry (GC/MS), the filtrate obtained is esterified, since fatty acids cannot be analysed using this type of method. 100 mg of Amberlyst® 15 (dry, Ref. 79291 STREM Chemicals) are therefore added to the filtrate which is then refluxed for two hours.

The medium is then filtered to remove the Amberlyst® 15 (dry, ref 79291, STREM Chemicals), and the filtrate is evaporated at reduced pressure. This produces the mixture of esters expected for analysis with a quantitative yield (2.34 g) of a mixture having the same proportions of pelargonic acid and azelaic acid in ester form.

GC/MS analysis of the esters obtained, after esterification according to the method previously described, confirms the presence of the products with 100% selectivity and a GC yield of 100% mono or di-carboxylic acid.

The following table lists the results obtained:

| Input | Time (h) | Temperature (° C.) | Conversion (%) | GC proportion % A/B/C/D |
|---|---|---|---|---|
| 1 | 15 | 140 | 100 | 48/44/4/4 |

The GC percentages in the above table and in the following tables are expressed by weight.

EXAMPLE 2

Synthesis of carboxylic acid from 1,2-octanediol acid, by oxidative cleavage

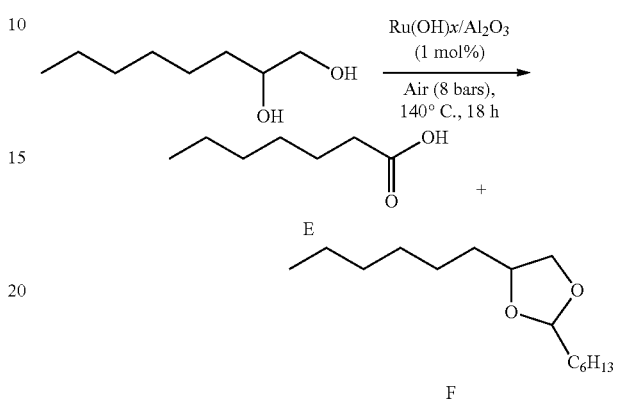

2 g (mmol) of 1.2-octanediol are added in the presence of 1 mol % of Ru(OH)$_x$/Al$_2$O$_3$ (1≤x≤3) in an autoclave. This catalyst is identical to that used in example 1.

The mixture is then heated to 140° C. for 18 h at 8 bar air pressure. After 15 h, the reaction medium is diluted in 10 mL of methanol then filtered. After evaporation of the organic phase, 2 g of products are obtained.

GC/MS analysis confirms the presence of products with 90% conversion.

The following table lists the results obtained:

| Input | Conversion % | GC proportion % E/F |
|---|---|---|
| 1 | 90 | 3/54 |

The product F is obtained with selectivity higher than 90%, which corresponds to the aldehyde obtained by oxidative cleavage of the diol protected by the diol itself.

EXAMPLE 3

Synthesis of mono- and di-carboxylic acid from 9,10-dihydroxystearate acid, by oxidative cleavage

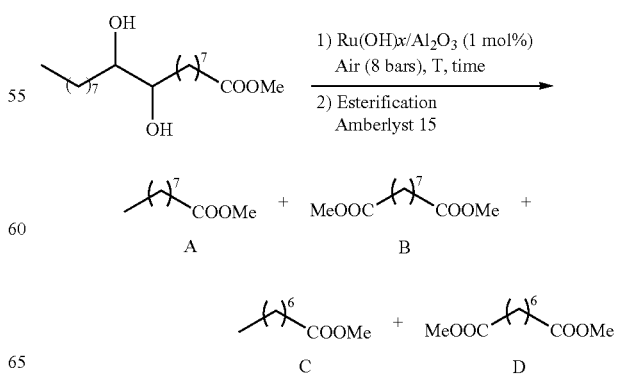

8 g of methyl 9,10-dihydroxystearate, obtained by the method described in example 1a applied to 75% technical grade commercial methyl oleate are added in the presence of 1 mol % of Ru(OH)$_x$/Al$_2$O$_3$ (1≤x≤3) in an autoclave.

The catalyst Ru(OH)$_x$/Al$_2$O$_3$ is identical to that used in examples 1 and 2.

The mixture is then heated to 150° C. for 15 h at 8 bar air pressure. After 15 h, the reaction medium is diluted in 40 mL of methanol then filtered.

To allow analysis, the filtrate is then esterified. 400 mg of Amberlyst 15 (STREM Chemicals) are therefore added to the filtrate obtained which is then refluxed for two hours.

The medium is filtered to remove the Amberlyst 15 (STREM Chemicals), then the filtrate is evaporated at reduced pressure. A mixture containing the same proportions (wt/mol) of pelargonic acid and azelaic acid is then obtained in the form of the ester expected (8.82 g) with 94% diol conversion. GC/MS analysis (after esterification according to the method previously described) confirms the presence of products with 93% selectivity.

The following table lists the results obtained:

| Input | Time (h) | Temperature (° C.) | Conversion (%) | GC proportion % A/B/C/D |
|---|---|---|---|---|
| 1 | 15 | 120 | 94 | 44/47/2/2 |

The invention is not limited to the embodiments described and other embodiments will be clearly apparent to those skilled in the art.

The invention claimed is:

1. Method for preparing a carboxylic acid, by oxidative cleavage of at least one vicinal diol, or an epoxide, the reaction being conducted in the presence of a catalyst based on ruthenium or molybdenum, an oxidizing agent and in the absence of solvent, wherein the oxidizing agent is oxygen contained in air.

2. Method according to claim 1, wherein the catalyst used has the formula M(OH)x/support, M being a metal selected from the group consisting of ruthenium, molybdenum, and a mixture thereof, and x is an integer from 0 to 8.

3. Method according to claim 2, wherein the support is selected from the group consisting of alumina, zirconia, carbon, silica, a zeolite and a mixture thereof.

4. Method according to claim 2, wherein M is ruthenium.

5. Method according to claim 4, wherein the proportion of metal used is from 0.001 mol % to 50 mol % relative to the substrate and from 0.001% to 50% relative to the support.

6. Method according to claim 1, wherein the reaction is conducted at a pressure from $10^{-3}$ mbar to 15 bar.

7. Method according to claim 1, wherein the reaction is conducted at a temperature from 0° C. to 200° C.

8. Method according to claim 1, wherein the vicinal diol or the epoxide is also a fatty acid or a fatty acid ester with a carbon chain of 10 to 30 carbon atoms.

9. Method according to claim 8, wherein the fatty acid or fatty acid ester is selected from the group consisting of myristoleic acid, palmitoleic acid, oleic acid, ricinoleic acid, gadoleic acid, erucic acid, nervonic acid, linoleic acid, alpha-linolenic acid, gamma-linolenic acid, di-homo-gamma-linolenic acid, arachidonic acid, timnodonic acid, and cervonic acid.

10. Method according to claim 1, wherein the vicinal diol is 9,10-dihydroxystearic acid or cyclohexane diol.

11. Method according to claim 1, for preparing a saturated or unsaturated dicarboxylic acid.

12. Method according to claim 1, for preparing an unsaturated carboxylic acid.

13. Method according to claim 1, wherein the products obtained are pelargonic acid and azelaic acid.

14. Method according to claim 1, wherein the reaction is conducted at a pressure from 4 bar to 10 bar.

15. Method according to claim 1, wherein the reaction is conducted at a temperature from 90° C. to 160° C.

* * * * *